US007910054B1

(12) United States Patent
Kaiser

(10) Patent No.: US 7,910,054 B1

(45) Date of Patent: Mar. 22, 2011

(54) DECONTAMINATION AND/OR CLEANING OF FRAGILE MATERIALS

(75) Inventor: Robert Kaiser, Winchester, MA (US)

(73) Assignee: Argos Associates, Inc., Winchester, MA (US)

( * ) Notice: Subject to any disclaimer, the term of this patent is extended or adjusted under 35 U.S.C. 154(b) by 1000 days.

(21) Appl. No.: 11/738,489

(22) Filed: Apr. 21, 2007

Related U.S. Application Data

(63) Continuation-in-part of application No. 11/451,294, filed on Jun. 12, 2006, now Pat. No. 7,494,629, which is a continuation-in-part of application No. 10/154,428, filed on May 23, 2002, now abandoned.

(60) Provisional application No. 60/293,016, filed on May 23, 2001.

(51) Int. Cl.
*A61L 2/16* (2006.01)

(52) U.S. Cl. ............................ 422/28; 442/121; 134/42

(58) Field of Classification Search ................ 422/1, 28; 401/40, 49, 196; 134/42; 442/121, 122, 442/123
See application file for complete search history.

(56) References Cited

U.S. PATENT DOCUMENTS 2,933,453 A 4/1960 Burks, Jr.
3,874,849 A 4/1975 Teng et al.
4,842,746 A 6/1989 Fowler et al.
4,847,089 A 7/1989 Kramer et al.
4,850,729 A 7/1989 Kramer et al.
4,928,681 A 5/1990 Langston et al.
5,079,792 A 1/1992 D'Haen
5,230,960 A 7/1993 Iizuka
5,264,044 A 11/1993 Li
5,695,775 A 12/1997 Von Blucher et al.
5,938,858 A 8/1999 Yokoyama et al.
6,053,952 A 4/2000 Kaiser
6,156,407 A 12/2000 Neubauer et al.
(Continued)

FOREIGN PATENT DOCUMENTS

BE 903622 A 3/1986
(Continued)

OTHER PUBLICATIONS

"Decontamination Kit, Individual Equipment: M295", SBC COM online, http://sbccom.apgeo.army.mil/products/m295.htm, May 2, 2000, 2 pages.

(Continued)

*Primary Examiner* — Sean E Conley
(74) *Attorney, Agent, or Firm* — Cesari and McKenna, LLP

(57) ABSTRACT

In one embodiment, contaminates are removed from a material by contacting an activated carbon fabric wetted with a solvent with the surface of the material. The activated carbon fabric is maintained in contact with the surface in a substantially vapor-tight environment to allow the solvent to dissolve the contaminants, the contaminates to diffuse in the solvent, and the contaminates to be adsorbed by the activated carbon fabric. Thereafter, the activated carbon fabric containing the contaminates is removed and the any remaining solvent is allowed to evaporate. In another embodiment, contaminates are removed from a material by maintaining a solvent wetted fabric in contact with the surface of a material, while exposing at least an upper face of the fabric to a surrounding environment to promote evaporation of the solvent. The evaporation of the solvent from the upper face migrates contaminates from the surface into the fabric where they are contained.

27 Claims, 6 Drawing Sheets

U.S. PATENT DOCUMENTS

| | | | | |
|---|---|---|---|---|
| 6,269,513 | B1 * | 8/2001 | Torobin | 15/104.93 |
| 6,375,976 | B1 | 4/2002 | Roden et al. | |

FOREIGN PATENT DOCUMENTS

| | | | |
|---|---|---|---|
| EP | 0053936 | B1 | 4/1989 |
| JP | 09111653 | A | 4/1997 |

OTHER PUBLICATIONS

"M291 Skin Decontamination Kit", SBC COM online, http://sbccom.apgeo.army.mil/products/m291.htm, May 11, 2000, 1 page.

Dr. Stephen Thomas, Bruce Fisher, Paul Fram, & Dr Mike Waring, "Odour Absorbing Dressings: A comparative laboratory study", World Wide Wounds—The Electronic journal of wound management practice, http://smtl.co.uk/World-Wide-Wounds/1...-Dressings/odour-absorbing-dressings.html, Jul. 3, 1998, 11 pages.

"Sorbent Decontamination Systems (SDS)", SBC COM online, http://sbccom.apgeo.army.mil/RDA/sds/index.htm, Sep. 19, 2000, 4 pages.

"Sorbent Decontamination System, XM100", SBC COM online, http://sbccom.apgeo.army.mil/products/sds.htm, Sep. 19, 2000, 1 page.

Peter Zvirble & Albert A. Koadritner, "Studies On Skin Decontamination", Chemical Corps Medical Laboratories Research Report, Jun. 1953, 17 pages.

"Wound and Skin Care", CarboFlex, http://www.convatec.com/wound2/whatsnew/carbofl.htm, Nov. 9, 1999, pp. 1-2.

"S.M.T.L. Dressing Data Cards," http://www.smtl.co.uk/WMPRC/DataCards/HTML/, Dec. 16, 1997, 11 pages.

C. Van Hooidonk, B.I. Ceulen, J. Bock, and J. Van Genderen, "CW Agents and the Skin Penetration and Decontamination", Proc. Int. Symp. Protection Against Chemical Warface Agents, Stockholm, Sweden, Jun. 6, 1983, pp. 153-160.

Dr. Ming-Houng (Albert) Chang, Dr. Alex Ciegler, Dr. Roy Crochet, "A Survey and Evaluation of Chemical Warfare Agent-decontaminants and Decontamination" Defense Information Systems Agency, U.S. Department of Defense, Oct. 15, 1984, 82 pages.

Albert M.H. Chang, Ph.D. and Alex Ciegler, Ph.D "Chemical Warfare: Part I: Chemical Decontamination" vol. 1, No. 4, Oct. 15, 1984, pp. 59-65.

"Health Service Support In a Nuclear, Biological, and Chemical Environment" Field Manual FM 9-10-7, Headquarters, Department of the Army, Nov. 9, 1999, 19 pages.

"Thermal Management Fluids and Services", 3M Fluorinert Electronic Liquid, 3M Novec Engineered Fluids, Jun. 2000, 4 pages.

"A High-Performance Heat Transfer Fluid with Favorable Environment Properties" 3M Novec Engineered Fluid HFE-750, Jun. 2000, 11 pages.

Phillip Tuna, Lew Tousignant, "Reducing Emissions of PFC Head Transfer Fluids" EHS Challenges and Analytical Methodologies session at the SEMI Technical Symposium, Jul. 16, 8 pages, published: Mar. 2002.

Yam, C.S. et al., Abstract of "Enhanced Removal of Radioactive Particles from Circuit Boards by Flourinated Surfactant Solutions," Proceedings of the Annual Meeting of the Adhesion Society, 1995, $18^{th}$, pp. 62-65.

* cited by examiner

DECONTAMINATION AND/OR CLEANING OF FRAGILE MATERIALS

RELATED CASES

The present application is a continuation-in-part of U.S. patent application Ser. No. 11/451,294 now U.S. Pat. No. 7,494,629 entitled "Decontamination System and Method of Decontamination," filed on Jun. 12, 2006, which itself is a continuation-in-part of U.S. patent application Ser. No. 10/154,428, now abandoned entitled "Decontamination System and Method of Decontamination," filed on May 23, 2002, and which claims priority from U.S. Provisional Patent Application No. 60/293,016, which was filed on May 23, 2001 for a "Decontamination System and Methods of Decontamination."

BACKGROUND

1. Field of the Disclosure

The present disclosure relates generally to decontamination and/or cleaning, and more specifically to decontamination and/or cleaning of fragile materials, for example certain historic artifacts.

2. Background Information

Decontamination and/or cleaning of materials typically involves the application of a solvent along with substantial mechanical energy, for example, mechanical energy in the form of shear caused by a high pressure spray, a stirred or ultrasonic bath, mechanical scrubbing, or other techniques. The application of mechanical energy generally causes the removal of contaminates by convective mass transfer.

However, many conventional decontamination and/or cleaning techniques are unsuited for cleaning fragile materials, for example, delicate historic artifacts such as textiles, skins, papers, and other frail items. These types of historic artifacts are often mechanically fragile, and thus respond adversely to high pressure spraying, stirred or ultrasonic baths, mechanical scrubbing and other aggressive techniques. Similarly, such historic artifacts are often incompatible with many solvents, as the solvents may remove, in addition to the undesired contaminates, desired pigments, dyes, inks, paints, stains, and/or other types of substances present on the artifact. Due to the typically high monetary and cultural value of historic artifacts, even very minor damage due to decontamination and/or cleaning is generally deemed unacceptable.

Yet the need to decontaminate and/or clean fragile materials, such as delicate historic artifacts, still exists despite the challenges the process presents. In addition to cleaning rather innocuous contaminates from artifacts for largely aesthetic reasons, decontamination and/or cleaning may be needed to remove toxic contaminates that are potentially harmful to people handling the artifacts. Some historic artifacts are contaminated from the environment in which they were discovered or historically maintained. More often, historic artifacts have been unintentionally contaminated by museum personnel or others, who applied toxic chemicals to the artifacts in preservation efforts.

In the nineteenth and early twentieth century many historic artifacts in museum collections were treated with a variety of pesticide, fungicides, and other preservative agents. For example, during the ninetieth and early twentieth centuries tobacco, camphor, strychnine, carbolic acid, sulfur, mercuric chloride, thymol, naphthalene, and several forms of arsenic were often used for preservation. In the later half of the twentieth century other types of chemicals were often used, including various organochlorides (such as DDT and lindane), organophosphates (such as malathion), and organometallic compounds (such as methyl mercury acetate and or triethyl arsine). These chemicals were often liberally brushed, sprayed, and/or sprinkled onto the surfaces of the historic artifacts. Despite the passage of time, many historic artifacts in museum collections are still highly contaminated with toxic residues from these chemicals. Prolonged exposure to the artifacts may cause any of a variety of maladies to exposed persons. This hazard hinders the work of museum personnel and researchers, who need to handle the artifacts to create exhibits or to study the artifacts. Similarly, this hazard inhibits the return of some historic artifacts to native peoples who may have legal rights to the artifacts.

Accordingly, there is a need for techniques to decontaminate and/or clean fragile materials, such as delicate historic artifacts, that address their special needs, while effectively decontaminating and/or cleaning the materials.

SUMMARY

A fragile material, such as a delicate historic artifact, may be decontaminated and/or cleaned by novel diffusion cleaning and/or evaporative cleaning techniques.

In one embodiment, diffusion cleaning is conducted by first wetting a piece of activated carbon fabric with a solvent for the contaminates. The solvent used to wet the activated carbon fabric is preferably chosen to be compatible with the fragile material, such that contaminates to be removed are soluble in the solvent, yet pigments, dyes, inks, paints, stains, and/or other types of substances desirably present on the fragile material are not soluble in the solvent, and thus not removed. Depending on the particular application, the contaminates may be rather innocuous substances whose removal is desired for largely aesthetic reasons and/or more toxic substances, for example pesticides, fungicides, and other preservative agents, that that are potentially harmful to people handling the artifacts.

The wetted activated carbon fabric is brought into contact with the surface of the fragile material in a substantially vapor-tight environment. In some configurations, a weight is applied to the upper face (i.e., the face not contacting the fragile material) of the activated carbon fabric, to promote full contact between the fabric and the fragile material. The solvent dissolves the contaminates present on the surface of the fragile material. Thereafter, the contaminates molecularly diffuse in the solvent and are thereafter adsorbed by the activated carbon fabric, with operates as an adsorptive blotter. The process of molecular diffusion and adsorption typically requires extended periods of time, in some cases on the order of 24 hours to 120 hours. Adsorption into the activated carbon fabric substantially depletes the contaminates (or at least a portion of the contaminates to be removed in a current round of diffusion cleaning) from the surface of the fragile material. The now contaminated activated carbon fabric is removed and any remaining solvent present on the surface of, or adsorbed into, the material is allowed to evaporate.

Further, in some embodiments, evaporative cleaning may be employed in addition to, or rather than, diffusion cleaning. Evaporative cleaning may be conducted by maintaining solvent-wetted activated carbon fabric (or other type of fabric) in contact with the fragile material while evaporation takes place. At least the upper face of the activated carbon fabric (or other type of fabric) is exposed to the surrounding environment. As the solvent evaporates from the upper face of the activated carbon fabric (or other type of fabric), a substantial portion of the contaminates migrate from the surface of the fragile material into the activated carbon fabric (or other type of fabric), where they become captured and contained. After the solvent has substantially fully evaporated, the now contaminated activated carbon fabric (or other type of fabric) is removed. In some embodiments, a weight is applied to some portion of the upper face of the activated carbon fabric (or other type of fabric), to promote contact with the material.

As discussed below a variety of modifications and additions may be made to these embodiments.

BRIEF DESCRIPTION OF THE DRAWINGS

The description below refers to the accompanying drawings, of which.

DETAILED DESCRIPTION OF ILLUSTRATIVE EMBODIMENTS

Figure 1:
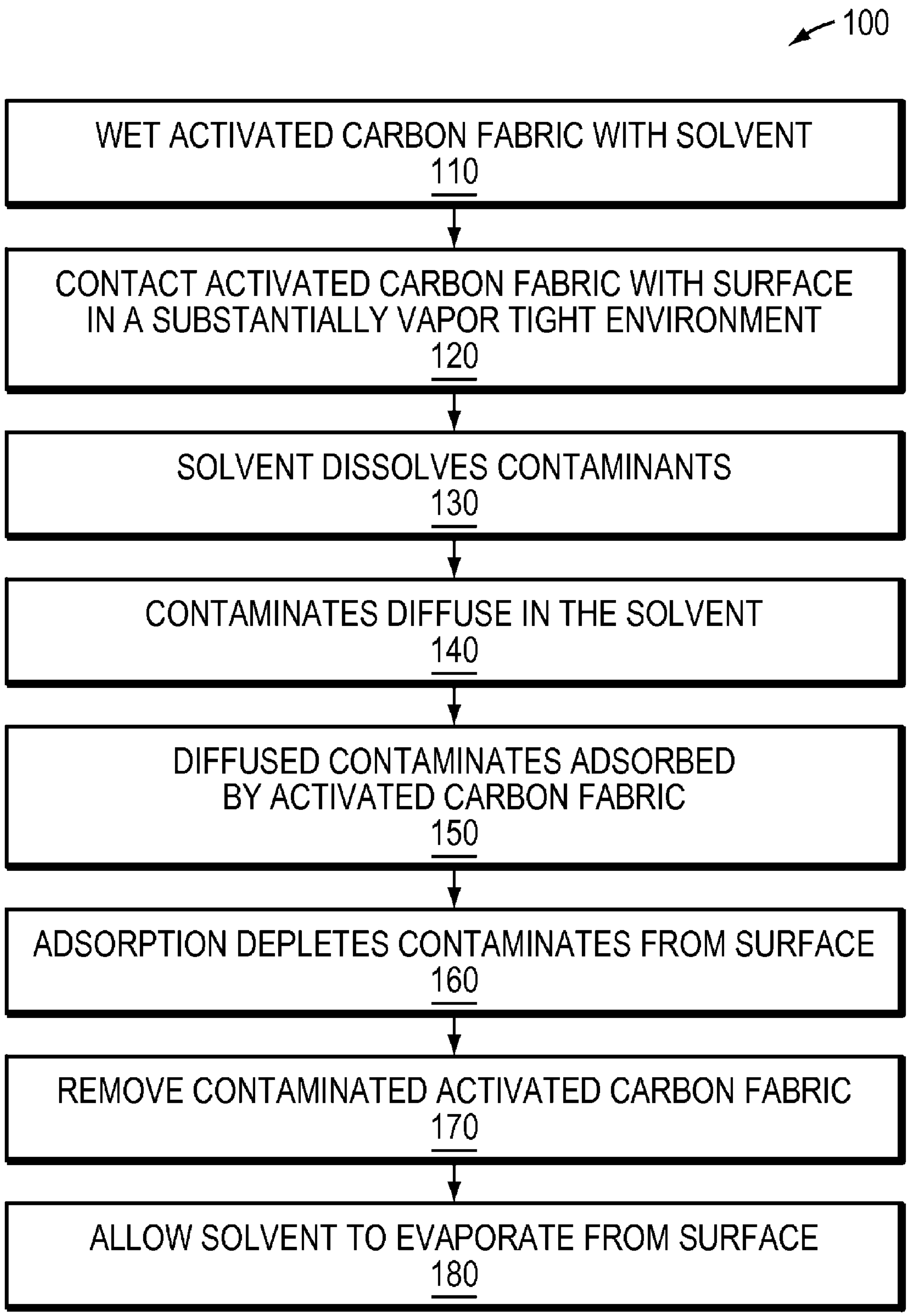
FIG. 1 is a flow diagram showing an example sequence of steps for decontaminating and/or cleaning the surface of a fragile material, such as a delicate historic artifact, utilizing diffusion cleaning.
Figure 2:
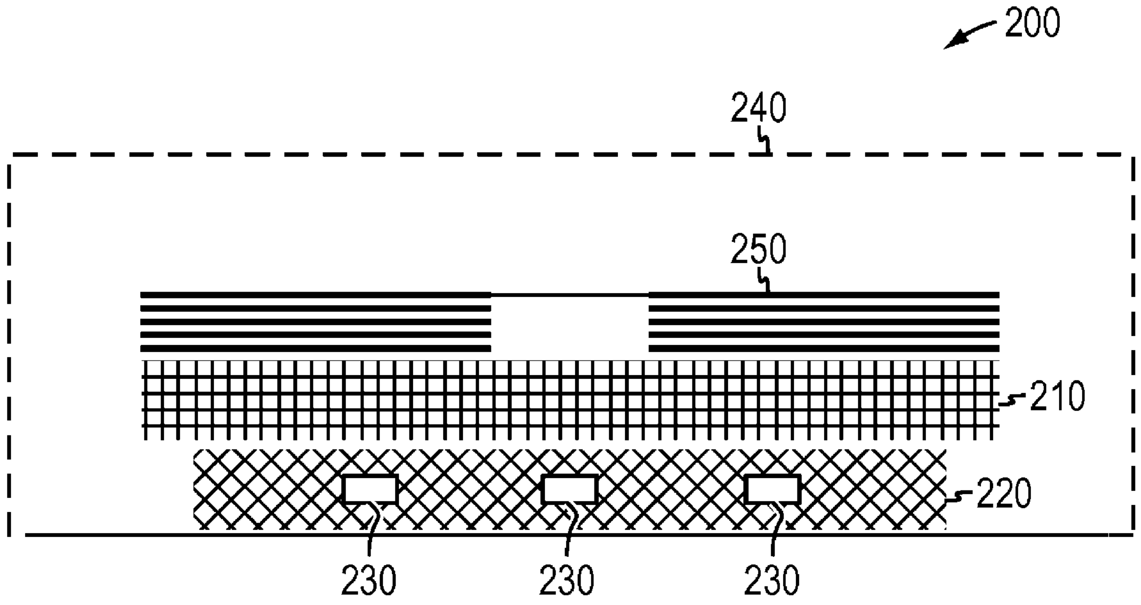
FIG. 2 is a schematic diagram of an example arrangement for diffusion cleaning of the surface of a fragile material.

FIG. 1 is a flow diagram 100 showing an example sequence of steps for decontaminating and/or cleaning the surface of a fragile material, such as a delicate historic artifact, utilizing diffusion cleaning. FIG. 2 depicts an example arrangement 200 for diffusion cleaning of the surface of a fragile material 220 that may be used in performing the steps shown in FIG. 1.

At step 110, a piece of activated carbon fabric 210 sufficiently sized to cover a piece of fragile material 220 is wetted with a solvent. Activated carbon fabric 210 (i.e., activated carbon woven, bonded or otherwise integrated into a textile form) is commercially available from a number of vendors, for example Charcoal Cloth International Ltd., which markets different such fabrics under the trade name Zorflex®. The designations and properties of several representative Zorflex® activated carbon fabrics are given in the following table:

TABLE 1

Properties of Zorflex ® Activated Carbon Fabrics

| Fabric Designation | FM 10 | FM 70 | FM 100 | FM 50K |
|---|---|---|---|---|
| Construction | 1/1 plain weave | Compound Weave | 1/1 double weave | Double jersey (knit) |
| Surface Density, $g/m^2$ | 120 | 190 | 240 | 130 |
| Tensile Strength,, kg/cm | | | | |
| Warp | 1.0 | 2.5 | 2.0 | 0.7 |
| Waft | 1.5 | 2.0 | 2.0 | 0.8 |
| Ethyl Acetate Uptake, wt-% | | | | |
| min | 30 | 30 | 30 | 30 |
| max | 40 | 40 | 40 | 40 |
| Air Permeability (*) | 130 | 75 | 75 | 75 |
| Thickness, mm | 0.5 | 0.8 | 1.0 | 0.4 |

(*) $cm^3/cm^2/sec$ at 10 mm water gauge

It is expressly contemplated that any of a wide variety of activated carbon fabrics may be employed, and, as such, the techniques described herein are in no way limited to this the specific activated carbon fabrics enumerated in Table 1.

Further, in some embodiments a combination of two or more fabrics may be employed, with such fabrics laminated, bonded or otherwise integrated together. For example, in one embodiment, a laminate of Zorflex® FM 50K activated carbon fabric and Zorflex® FM 100 activated carbon fabric may be employed. Similarly, in another embodiment, a laminate of a Zorflex® activate carbon fabric and a non-adsorptive facing fabric may be employed. Accordingly, when the term "activated carbon fabric" is used herein the term should be interpreted broadly to encompass many different fabrics and/or combinations of fabrics.

The solvent used to wet the activated carbon fabric 210 is preferably chosen to be compatible with the fragile material, such that contaminates 230 to be removed are soluble in the solvent, yet desired pigments, dyes, inks, paints, stains, and/or other types of substances present on the material are not soluble in the solvent. Similarly, the solvent is preferably chosen as one that does not cause physical damage to the structure of the material, for example, does not cause the material to become brittle, wrinkled, or otherwise adversely affected. In one embodiment, the solvent may be 3M™ Novec™ Engineered Fluid HFE-7200 otherwise known as ethoxy-nonafluorobutane ($C_4F_9OC_2H_5$) (hereinafter referred to as "HFE-7200"), commercially available from 3M Corp. HFE-7200 is typically compatible with a wide variety of substances that may be found in historic artifacts, yet easily dissolves many toxic contaminates, such as malathion and other organophosphate pesticides, as well as methyl mercury acetate, triethyl arsine, and other organometallic compounds. In alternate embodiments, a variety of other solvents may be employed, for example Novec™ 3M™ Engineered Fluid HFE-7100 otherwise known as methoxy-nonafluorobutane ($C_4F_9OCH_3$) (hereinafter referred to as "HFE-7100"), commercially available from 3M Corp., or any of a variety of other solvents appropriate for the application.

At step 120, the now wetted activated carbon fabric 210 is brought into contact with the surface of the fragile material 220 in a substantially vapor-tight environment 240. In some cases, additional solvent may applied directly to the fragile material 220.

The vapor-tight environment 240 may be achieved in a number of ways. For example, the vapor-tight environment 240 may be a sealed plastic bag or other container that is substantially air-tight. Alternately, the activated carbon fabric 210 may be covered with a vapor barrier (or the activated carbon fabric 210 may have an integrated vapor barrier) to create a substantially vapor-tight environment 240 between a solid surface on which the fragile material is resting, such as a table top, and the vapor barrier.

In some embodiments, a weight 250, for example, a metal plate or other object, is applied to the upper face (i.e., the face not contacting the fragile material) of the activated carbon fabric 210, to promote full contact of the fabric with the fragile material 220, thereby minimizing air gaps between the two. Alternately, contact may be promoted by pressure applied by a device, for example, a clip or arm (not shown), that holds the activated carbon fabric 210 in contact with the surface of the fragile material 220.

At step 130, the solvent dissolves the contaminates 230 present on the surface of the fragile material 220. As discussed above, depending on the particular application, the contaminates 230 may be rather innocuous substances whose removal is desired for largely aesthetic reasons and/or more toxic substances, for example pesticides, fungicides, and other preservative agents, that are potentially harmful to people handling the artifacts. At step 140, the contaminates 230 molecularly diffuse in the solvent. At step 150, the contaminates 230 are adsorbed, by the activated carbon fabric 210, with operates as an adsorptive blotter. The process of molecular diffusion and adsorption in steps 140 and 150 typically requires extended periods of time, during which the molecules of the contaminates 230 slowly make their way through the solvent. The exact period of time required depends on the nature of the fragile material 220, the particular contaminates 230 present, the solvent, the environment, and a variety of other factors. Accordingly, while in some embodiments the time period may be on the order of 24 hours to 120 hour, a variety of other time periods are expressly contemplated.

Further, in some cases during the extended period of time the activated carbon fabric 210 and/or the surface of the fragile material 220 may be re-wetted with solvent. Re-wetting is desirable should the solvent appear to evaporate significantly despite the substantially vapor-tight environment 240, leaving the activated carbon fabric 210 and/or the surface of the fragile material 220 dry.

At step 160, adsorption into the activated carbon fabric 210 substantially depletes the contaminates (or at least a portion of the contaminates to be removed in a current round of diffusion cleaning) from the surface of the fragile material 220. Through adsorption the activated carbon fabric 210 captures and contains the contaminates 230 as well as at least a portion of the solvent used in the decontamination and/or cleaning process. At step 170, the now contaminated activated carbon fabric 210 is removed and disposed of, for example, by sending the contaminated fabric to an appropriate waste disposal facility. Any remaining solvent present on the surface of, or adsorbed into, the fragile material 220 is allowed to evaporate. The material 220 may be removed from the vapor-tight environment 240 and exposed to the surrounding environment, for example exposed to the free-moving air of a room, placed under a fume hood, or placed in some other space to promote evaporation. If additional decontamination and/or cleaning is desire, the above described sequence of steps 110-180 may be repeated.

Figure 3A:
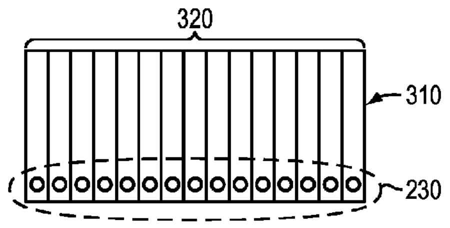
FIGS. 3*a*-3*h* are schematic diagrams of an example progression of diffusion cleaning of a porous surface of a fragile material.
Figure 3B:
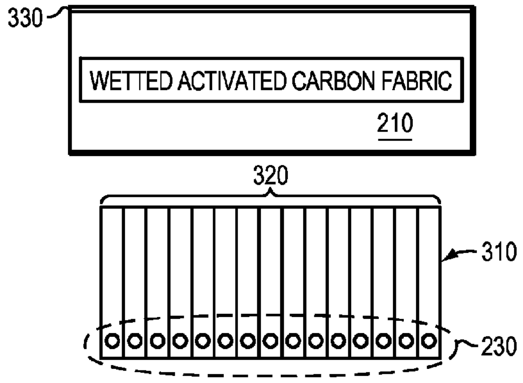
Figure 3C:
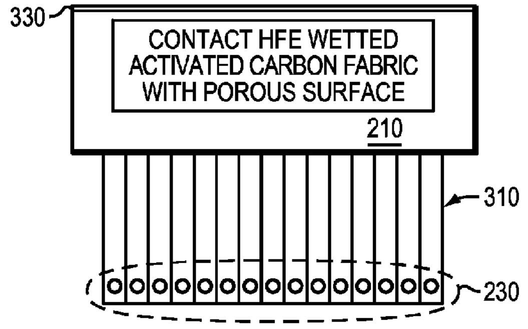
Figure 3D:
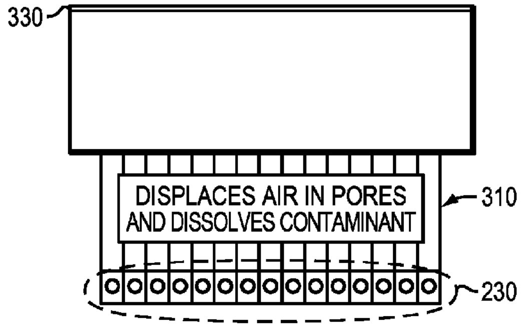
Figure 3E:
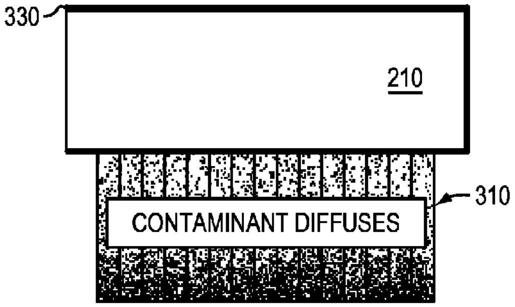
Figure 3F:
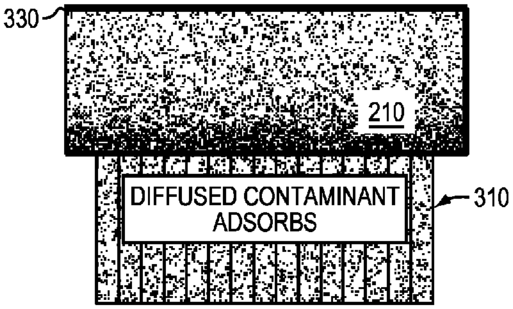
Figure 3G:
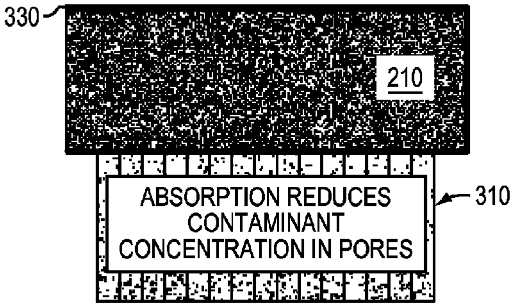
Figure 3H:
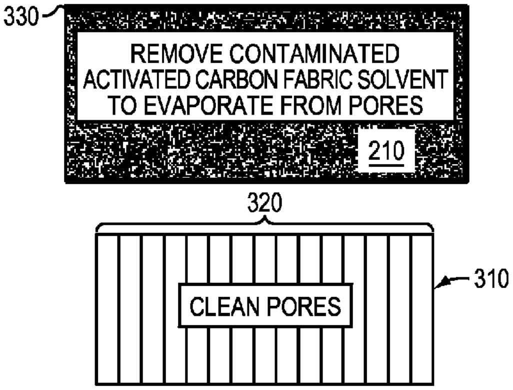

FIGS. 3*a*-3*h* are schematic diagrams of an example progression of diffusion cleaning of a porous surface 310 of a fragile material. The progression provides a more specific example of an application of the techniques described above in reference to FIG. 1. In FIG. 3*a*, a porous surface 310 includes a plurality of pores 320. Various contaminates 230, such as organophosphates, may be disposed in the pores 320. As shown in FIG. 3*b*, an activated carbon fabric 210 may be wetted with a solvent, for example HFE-7200. In some configurations, a vapor barrier 330 may be affixed or integrated into the activated carbon fabric, to substantially prevent evaporation of the solvent. As shown in FIG. 3*c*, the activated carbon fabric 210 is contacted with the porous surface 310. In FIG. 3*d*, the solvent displaces air in the pores of the porous surface 310, and dissolves the contaminates 230. As shown in FIG. 3*e*, the contaminates diffuse over time in the solvent, contaminating the solvent while spreading through the porous surface 310. The contaminates in the solvent are adsorbed over time into the activated carbon fabric 210, as depicted in FIG. 3*f*. FIG. 3*g* shows that the concentration of contaminates in the pores of the porous surface 310 is reduced as contaminates are adsorbed into the activated carbon fabric 210. In FIG. 3*h*, after the adsorption of the contaminates has substantially depleted the contaminates from the pores, the activated carbon fabric 210 may be removed and disposed of in an appropriate manner. Any solvent still present in the now substantially clean pores 320 may be allowed to evaporate, thus completing the progression.

While the above described diffusion cleaning techniques may be advantageously employed to decontaminate and/or clean the surface of a fragile material, in certain instances evaporative cleaning may be employed in addition to, or rather than, diffusion cleaning. For example, a preferred solvent that is highly compatible with a certain fragile material may contain components that interfere with the adsorption of some contaminates into activated carbon fabric, and thus may hinder the removal of some contaminates by diffusion cleaning. Accordingly, it may be desirable to first conduct a diffusion cleaning session and subsequently perform an evaporative cleaning session. For example, after step 160 of FIG. 1, where adsorption has depleted at least some of the contaminates 230 from the surface of the fragile material 220, evaporative cleaning may be performed. Alternately, it may be desirable to only conduct an evaporative cleaning session in certain cases.

Figure 4:
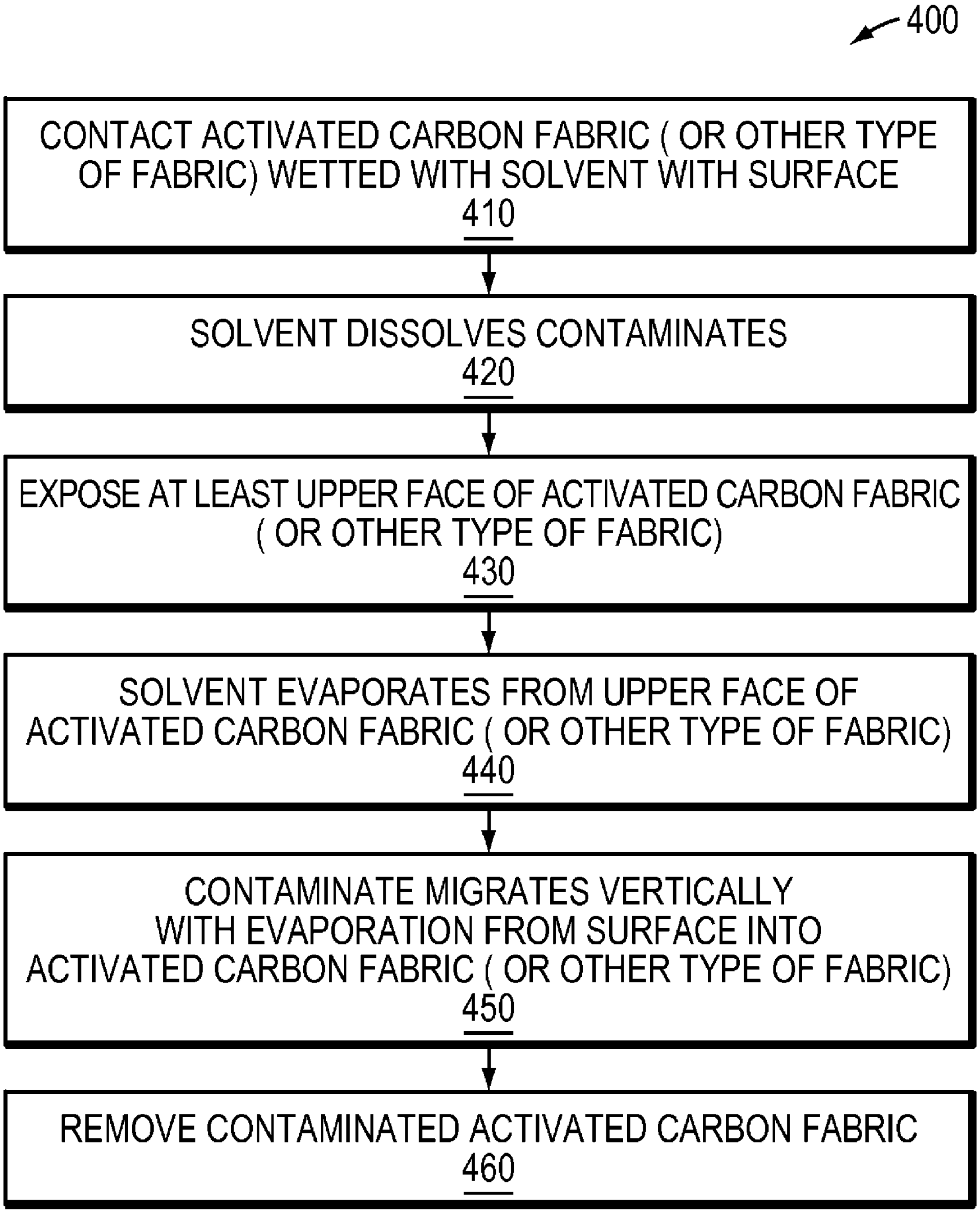
FIG. 4 is a flow diagram showing an example sequence of steps for decontaminating and/or cleaning the surface of a fragile material, such as a delicate historic artifact, utilizing evaporative cleaning.
Figure 5:
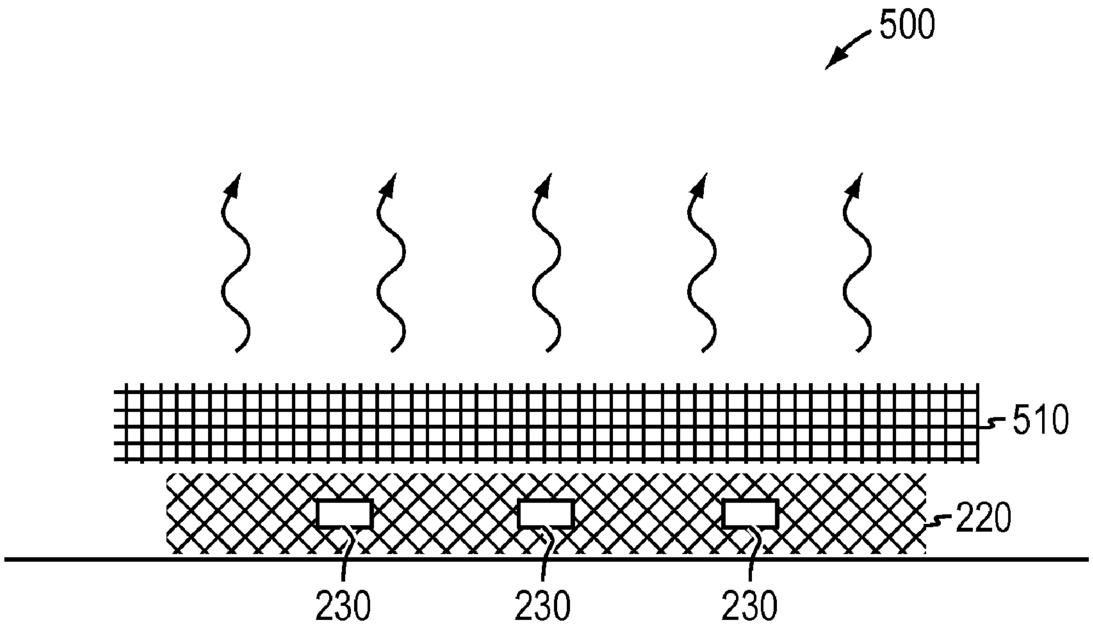
FIG. 5 is a schematic diagram of an example arrangement for evaporative cleaning of the surface of a fragile material.

FIG. 4 is a flow diagram 400 showing an example sequence of steps for decontaminating and/or cleaning the surface of a fragile material, such as a delicate historic artifact, utilizing evaporative cleaning. FIG. 5 is an example arrangement 500 for evaporative cleaning of the surface of a fragile material 220 that may be used in performing the steps shown in FIG. 4.

At step 410, a solvent-wetted activated carbon fabric (or other type of fabric, for example a gauze sponge) 510 is maintained in contact with the fragile material 220. In some cases, additional solvent may applied directly to the fragile material 220. The activated carbon fabric (or other type of fabric) 510 is wetted with a solvent in which the contaminates are soluble, yet which is compatible with the material to be decontaminated and/or cleaned. For example, the solvent may be HFE-7200, HFE-7100, or another suitable solvent. In some embodiments, a weight (not shown) is applied to some portion of the upper face of the activated carbon fabric (or other type of fabric) 510, to promote full contact with the fragile material 220. Alternately, contact may be promoted by pressure applied by a device, for example a clip or arm. Care should be taken, however, to ensure that any weight or device does not impede evaporation where decontamination and/or cleaning is desired.

At step 420, the solvent dissolves contaminates 230 present on the surface of the fragile material 220. At step 430, at least the upper face (i.e., the face not contacting the fragile material) of the activated carbon fabric (or other type of fabric) 510 is exposed to the surrounding environment, for example, exposed to the free-moving air of a room, placed under a fume hood, or placed in some other space to promote evaporation. At step 440, the solvent evaporates from the upper face of the activated carbon fabric (or other type of fabric) 510. At step 550, as the solvent evaporates, a substantial portion of the contaminates 230 migrate from the surface of the material 220 into the activated carbon fabric (or other type of fabric) 510, where they become captured and contained. At step 560, after the solvent has substantially fully evaporated, the now contaminated activated carbon fabric (or other type of fabric) 510 is removed and disposed of, for example, sent to an appropriate waste disposal facility. If additional decontamination and/or cleaning is desired, the sequence of steps 510-560 may be repeated.

The foregoing has been a detailed description of several embodiments. Further modifications and additions may be made without departing from the disclosure's intended spirit and scope. For example, while the above descriptions discuss fragile materials, for example delicate historic artifacts, the techniques disclosed herein are in no way limited to use only with fragile materials. They alternately may be applied to a variety of robust, sturdy, or otherwise non-fragile materials. Further, the techniques described above need not be applied in isolation, and it is expressly contemplated that they may be used in conjunction with other decontamination and/or cleaning techniques, as part of a multi-stage decontamination and/or cleaning process. Accordingly, it should be remembered that the above descriptions are meant to be taken only by way of example, and the invention is not restricted to any one particular embodiment, configuration or implementation discussed above. Rather, the invention is defined by the following claims.

What is claimed is:

1. A method for removing contaminates from a material comprising:

contacting an activated carbon fabric wetted with a solvent with the surface of the material;

maintaining the activated carbon fabric in contact with the surface of the material in a substantially vapor-tight environment for an extended period of time, the period of time sufficient to allow the solvent to dissolve the contaminants, the contaminates to diffuse in the solvent, and the contaminates to be adsorbed by the activated carbon fabric;

removing the activated carbon fabric containing the contaminates; and allowing any remaining solvent to evaporate from the material.

2. The method of claim 1 wherein the step of maintaining the activated carbon fabric in contact with the surface of the material further comprises:

placing a weight on the activated carbon fabric to promote contact with the material.

3. The method of claim 1 wherein the solvent comprises ethoxy-nonafluorobutane.

4. The method of claim 1 wherein the solvent comprises methoxy-nonafluorobutane.

5. The method of claim 1 wherein the material is mechanically fragile.

6. The method of claim 1 wherein the material is a historic artifact, and the contaminates comprise at least one organophosphate.

7. The method of claim 6 wherein the at least one organophosphate comprises malathion.

8. The method of claim 1 wherein the material is a historic artifact and the contaminates comprise at least one organometallic compound.

9. The method of claim 8 wherein the at least one organometallic compound comprises methyl mercury acetate.

10. The method of claim 8 wherein the at least one organometallic compound comprises triethyl arsine.

11. The method of claim 1 wherein the substantially vapor-tight environment material is a substantially air-tight environment.

12. The method of claim 11 the wherein the substantially air-tight environment is a sealed plastic bag.

13. The method of claim 1 the wherein the material is porous and the step of contacting further comprises:

displacing air in pores of the material with the solvent, to bring the solvent in contact with the contaminants.

14. The method of claim 1 wherein the period of time is greater than 24 hours.

15. The method of claim 1 wherein the activated carbon fabric is a laminate of two different activated carbon fabrics.

16. The method of claim 1 wherein the activated carbon fabric comprises a non-adsorptive facing fabric.

17. A method for removing contaminates from a material comprising:

contacting an activated carbon fabric wetted with a solvent with the surface of the material;

maintaining the activated carbon fabric in contact with the surface of the material in a substantially vapor-tight environment for an extended period of time, the period of time sufficient to allow the solvent to dissolve the contaminants, the contaminates to diffuse in the solvent, and the contaminates to be adsorbed by the activated carbon fabric;

removing the material and the activated carbon fabric from the substantially vapor-tight environment;

exposing at least an upper face of the activated carbon fabric to a surrounding environment to promote evaporation of the solvent, while still maintaining the activated carbon fabric in contact with the surface of the material, wherein the evaporation of the solvent migrates contaminates from the surface of the material into the fabric where they become contained; and when the solvent is fully evaporated, removing the activated carbon fabric containing the contaminates.

18. The method of claim 17, wherein the material is a historic artifact, and the contaminates comprise at least one organophosphate.

19. The method of claim 17, wherein the material is a historic artifact and the contaminates comprise at least one organometallic compound.

20. A method for removing contaminates from a material comprising:

contacting a fabric wetted with a solvent with the surface of the material;

maintaining the fabric in contact with the surface of the material while exposing at least an upper face of the fabric to a surrounding environment to promote evaporation of the solvent, wherein the evaporation of the solvent migrates contaminates from the surface of the material into the fabric where they become contained; and when the solvent is fully evaporated, removing the fabric containing the contaminates.

21. The method of claim 20 wherein the fabric is activated carbon fabric.

22. The method of claim 21 wherein the activated carbon fabric is a laminate of two different activated carbon fabrics.

23. The method of claim 21 wherein the activated carbon fabric comprises a non-adsorptive facing fabric.

24. The method of claim 20 wherein the step of maintaining the fabric in contact with the surface of the material comprises:

placing a weight on the fabric to promote contact with the material.

25. The method of claim 20 wherein the solvent comprises ethoxy-nonafluorobutane.

26. The method of claim 20 wherein the material is a historic artifact, and the contaminates comprise at least one organophosphate.

27. The method of claim 20 wherein the material is a historic artifact and the contaminates comprise at least one organometallic compound.

* * * * *